United States Patent [19]

Davis et al.

[11] Patent Number: 5,026,461
[45] Date of Patent: Jun. 25, 1991

[54] PROCESS FOR THE PREPARATION OF DODECANEDIOIC ACID

[75] Inventors: Darwin D. Davis; David L. Sullivan, both of Victoria, Tex.

[73] Assignee: E. I. Du Pont de Nemours and Company, Wilmington, Del.

[21] Appl. No.: 467,520

[22] Filed: Jan. 19, 1990

[51] Int. Cl.$^5$ .......................... C07C 5/00; C25B 3/02
[52] U.S. Cl. .................................. 204/86; 204/59 R; 204/78; 204/92; 204/93; 204/96; 204/129; 260/398.6; 562/544
[58] Field of Search .................... 204/59 R, 78, 92–93, 204/86, 96, 129; 260/398.6; 562/544

[56] References Cited

U.S. PATENT DOCUMENTS

| | | | |
|---|---|---|---|
| 3,459,644 | 8/1969 | MacLean et al. | 204/80 |
| 3,479,403 | 11/1969 | MacLean | 562/544 |
| 3,637,832 | 1/1972 | White et al. | 562/540 |
| 3,692,810 | 9/1972 | Washecheck | 562/544 |
| 4,532,079 | 7/1985 | Venturello et al. | 562/544 |
| 4,639,298 | 1/1987 | Kreh et al. | 204/78 |
| 4,794,172 | 12/1988 | Kreh | 204/78 |

OTHER PUBLICATIONS

Torii et al. "Indirect Electrooxidation of Alcohols and Aldehydes by Using a Double Mediatory System Consisting of $RuO_4/RuO_2$ and $Cl^+/Cl^-$ Redoxes in an Aqueous Organic Two-Phase System", J. Organic Chem.; 1986, vol. 51, pp. 155–161.

*Primary Examiner*—T. Tung
*Assistant Examiner*—David G. Ryser

[57] ABSTRACT

A process for the production of dodecanedioic acid by oxidation of cyclododecene using a two phase system in which ruthenium tetroxide serves as the oxidizing agent in the organic phase, and ruthenium tetroxide is regenerated in the second phase, an aqueous phase containing cerium ions in the plus 4 state. The cerium plus 4 ions may be regenerated by electrolytic oxidation in a separate step.

11 Claims, 1 Drawing Sheet

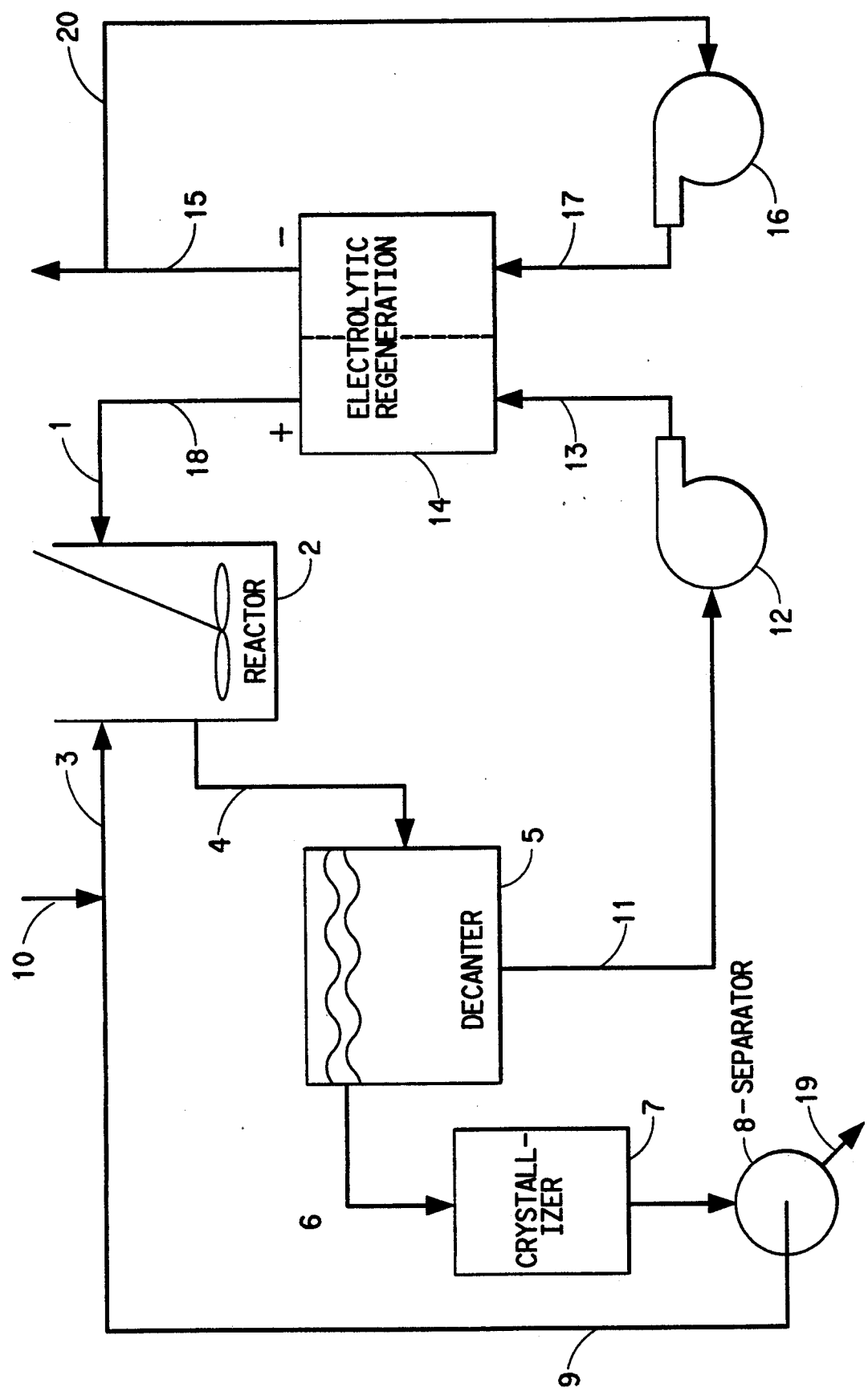

PROCESS FOR THE PREPARATION OF DODECANEDIOIC ACID

FIELD OF THE INVENTION

This invention relates to the production of dodecanedioic acid by the oxidation of cyclododecene. The oxidizing agent is ruthenium tetroxide. Ruthenium tetroxide is regenerated in the reaction mixture by cerium in the plus 4 oxidation state.

BACKGROUND OF THE INVENTION

Dodecanedioic acid is conventionally prepared by the air oxidation of cyclododecane thus forming cyclododecanol or cyclododecanone. These compounds are then oxidized to the acid by nitric acid. Such a process is disclosed in U.S. Pat. No. 3,637,832.

The oxidation of olefins to aldehydes, ketones and carboxylic acids by the use of ruthenium and cerium salt is disclosed in U.S. Pat. No. 3,459,644 to Mac Lean et al.

The oxidation of saturated cyclohydrocarbons to dioic acids using ruthenium tetroxide with a two-phase system in which the oxidation takes place in the organic phase and the ruthenium dioxide formed in the organic phase is oxidized to ruthenium tetroxide by sodium hypochlorite in the aqueous phase is disclosed in *J. Org. Chem.*, Vol. 40, No. 17, 1975 on pp. 2539–40 by Spitzer et al.

The oxidation of alcohols to carbonyl compounds using a two-phase system employing ruthenium tetroxide as the oxidizing agent in the organic phase, and in which the ruthenium dioxide formed is oxidized indirectly by electrolysis in the aqueous phase back to the tetroxide is disclosed in *J. Org. Chem.*, Vol. 51, pp. 155–161, (1986).

The electrolytic oxidation of cerium+3 ions to cerium+4 ions, and the use of cerium+4 ions as the oxidizing agent in the oxidation of aromatic compounds to carbonyl containing compounds in methanesulfonic acid is disclosed in U.S. Pat. No. 4,639,298 to Kreh.

SUMMARY OF THE INVENTION

The present invention is a process for the oxidation of cyclododecene to dodecanedioic acid and comprises the steps of forming a two-phase mixture comprising an aqueous phase containing cerium+4 ions, ruthenium tetroxide and at least one acid selected from the group consisting of methanesulfonic acid and sulfuric acid, and an organic phase containing ruthenium tetroxide and cyclododecene. In the mixture the mole ratio of cerium+4 ion to ruthenium tetroxide is greater than 1—preferably greater than 5. Cyclododecene and ruthenium tetroxide are soluble in the organic phase. In the organic phase cyclododecene is oxidized to dodecanedioic acid and ruthenium tetroxide is reduced to one or more suboxides including ruthenium dioxide, and its complexes. Ruthenium in its reduced state has limited solubility in the organic phase, and it tends to form a precipitate which is extracted or dissolved into the aqueous phase where it is oxidized by cerium+4 ions to ruthenium tetroxide, and the reformed ruthenium tetroxide is again dissolved in the organic phase where it reacts with additional cyclododecene. In order to assure that the cyclododecene is converted to the desired acid in high yield, and not aldehyde or other intermediate products, it is preferable that the mole ratio of ruthenium tetroxide to cyclododecene in the mixture should be greater than 1 during the oxidation part of the reaction. Finally, the $Ce^{+4}$/ruthenium ratio is allowed to fall below 1 at the end of the reaction in order to leave ruthenium in the reduced state and largely in the aqueous phase. The reaction mixture should be maintained at a temperature in the range of about 25° C. to 85° C. in order to assure efficient reaction with minimum undesired byproducts. The organic phase is then separated from the aqueous phase, and the dodecanedioic acid is separated from the organic phase by crystallization. The aqueous phase may be subjected to electrolytic oxidation to convert the cerium+3 ions to cerium+4 ions. The reduced ruthenium contained in the aqueous phase will at the same time be oxidized to ruthenium tetroxide.

An important advantage of this invention is that dodecanedioic acid produced in the oxidation is easily recovered from the organic phase with very little loss of ruthenium. Most of reduced ruthenium at the finish of the cyclododecene oxidation is present in the aqueous phase when the $Ce^{+4}$/ruthenium is less than 1, with only very small quantities of ruthenium in the organic phase.

The concentration of the ruthenium tetroxide in the two-phase mixture at the start of the reaction can vary from about 5 to 1300 parts by weight per million parts of the mixture.

The ratio of aqueous phase to organic acid phase in the reaction mixture is preferably in the range of 0.5 to 1 to 10 to 1.

The mole ratio of cerium+4 ion to ruthenium tetroxide in the two-phase reaction mixture can vary from 5 to 1 to 10,000 to 1 preferably 2,000 to 1.

The aqueous phase also contains methanesulfonic acid or sulfuric acid. Methanesulfonic acid or sulfuric acid is present in a concentration sufficient to keep the cerium ions soluble in the aqueous phase. Cerium salts, both +4 and +3 of methanesulfonic acid are more soluble than salts of other common acids. Preferably, the acid is methanesulfonic acid and the concentration in the two-phase mixture is about 1.5 to 9 molar.

DESCRIPTION OF THE DRAWINGS

The drawing is a flow diagram of the process for oxidizing cyclododecene to dodecanedioic acid.

DETAILED DESCRIPTION OF THE INVENTION

The overall process of converting cyclododecene to dodecanedioic acid is readily understood by reference to the Figure. An aqueous solution containing ruthenium tetroxide, cerium+4 ions and methanesulfonic acid, designated 1 in the Figure, is fed to stirred reactor 2. A solution of organic solvent, e.g. valeric acid and cyclododecene, 3, is also slowly fed to the reactor. The reactor is stirred so as to obtain a well-mixed two-phase system. After the reaction is complete, the contents of the reactor are passed via conduit 4 to decanter 5, where the organic phase is separated from the aqueous phase. The organic phase is passed via conduit 6 to crystallizer 7 and separator 8. The organic phase, e.g. valeric acid is then recycled via conduit 9 to where additional cyclododecene is added via conduit 10. The aqueous phase that is separated at decanter 5 plus make up water are passed via conduit 11 through pump 12 and conduit 13 to the anode compartment of electrolytic cell 14. The cathode compartment of cell 14 contains aqueous methanesulfonic acid which is recycled via conduit 15, pump 16, and conduit 17 with $H_2$ gas removed via conduit 20. The regenerated anolyte, now containing cerium in the +4 state as well as ruthenium tetroxide is recycled via conduit 18 to reactor 2. The crude dodecanedioic acid obtained at separator 8 is passed to a refining step via conduit 19.

If the process is operated in a continuous manner, the $Ce^{+4}$ to ruthenium ratio in the reactor is maintained at greater than 1 and a plug flow "clean up" reactor is added between reactor 2 and decanter 5, where the effluent from reactor 2 continues to react while the ratio of cerium+4 ion to ruthenium tetroxide is lowered to 1 or less. As an alternative to a clean up reactor, a reducing agent such as oxalic acid, or an aliphatic alkanol, e.g. methanol or an aldehyde may be added to the mixture to reduce $Ce^{+4}$ and any ruthenium tetroxide to suboxides and thus assure that the amount of ruthenium in the organic phase is very small. Reducing agent can also be added if needed when the process is operated batchwise. The amount of reducing agent employed should be sufficient to reduce the concentration of cerium in the plus 4 state in the reaction mixture to about zero, and the amount of ruthenium tetroxide to about zero.

The organic phase that serves as the solvent for the cyclododecene, the ruthenium tetroxide, and the dodecanedioic acid, must be insoluble or only slightly soluble in the aqueous phase, must be liquid under the conditions at which the process is practiced, must not be readily oxidized under the reaction conditions, and must be a poor or non-solvent for the lower oxides of ruthenium. Suitable materials for the organic phase include acids such as valeric acid, isovaleric acid, pivalic acid, isobutyric acid, 2-ethylbutyric acid, butyric acid, heptanoic acid, octanoic acid, and mixtures of such acids. Other classes of solvents have some of these properties and may be suitable to varying degrees. These include saturated hydrocarbons such as cyclohexane and hexane and the like and halogenated saturated hydrocarbons such as chloro and fluoro ethane, propane, etc.

EXAMPLES

Example 1

To a creased flask fitted with a paddle stirrer was added 70 ml of 0.33N $Ce(OSO_2CH_3)_4$ in 35.6% aqueous $CH_3SO_3H$. This solution was heated to 60° C. and 0.05 g ruthenium acetyacetonate plus 10 ml valeric acid was added while paddle stirring. After the reaction mixture turned yellow (ca 30 seconds), 0.086 g of cyclododecene was added dropwise over 3 minutes. The mixture was stirred an additional 5 minutes after completion of olefin addition, then decanted to yield a clear yellow valeric acid phase (5.8 g) and an aqueous phase (92 g). Analyses indicated cyclododecene was converted to dodecanedioic acid with 88% selectivity.

Example 2

To a 2-liter creased flask equipped with paddle stirring was added 1250 ml of 0.75N $Ce^{+4}$ present as cerium methanesulfonate ($Ce[SO_3CH_3]_4$) in 50% (wt/wt) aqueous methanesulfonic acid. This solution was heated to 60° C. and powdered ruthenium acetylacetonate (1.2231 g=3.07 ml) was added while stirring at about 500 rpm. During this addition, the green color associated with the reduced ruthenium disappeared and the yellow color of $RuO_4$ appeared as oxidation by $Ce^{+4}$ occurred. After the yellow color persisted, 225 ml of valeric acid was added to the flask.

Holding the reactor at 60° C. with 500 rpm stirring, a solution containing 12.1 g of cyclododecene (96% cyclododecene, 4% cyclododecane) in 25 ml valeric acid was added to the $RuO_4/Ce^{+\alpha}$ solution over 24 minutes. A 5 minute clean up time at 60° C. followed this, at which time the clear yellow valeric acid phase was removed and cooled to room temperature to yield 7.0 g of crude dodecanedioic acid.

Analyses of samples of the aqueous and organic phases from the reactor indicate about an 87% selectivity (95% conversion) from cyclododecene to product dodecanediooic acid or a 94% selectivity to the combined $C_{10}$, $C_{11}$, and $C_{12}$ dibasic acids present in both phases. Lower dibasic acids ($C_4$ through $C_9$) were the remaining cyclododecene oxidation products found. The aqueous mother liqour from the previously described $RuO_4/Ce^{+4}$ oxidation of cyclododecene was added to the anode reservoir of an electrolytic cell. An aqueous solution containing 50% (wt/wt) $CH_3SO_3H$ was added to the cathode reservoir of this electrolytic cell. After circulation (7.5 cm/sec velocity) to the anode and cathode for 15 minutes while maintaining an anode reservoir temperature of 50° C., a voltage of 2.1 to 2.2 volts was set between anode of platinum coated niobium and a stainless steel cathode while passing 5.0 amps between the 100 cm² electrodes.

Periodically removing the anolyte and titrating for $Ce^{+4}$ indicated the current efficiency (coulombs equivalent$^{-1}$ $Ce^{+4}$ theory/coulombs equivalent$^{-1}$ $Ce^{+4}$ actual×100) was 75-85% when the $Ce^{+3}$>0.1N.

We claim:

1. A process for oxidation of cyclododecene to dodecanedioic acid which comprises forming a mixture having an aqueous phase comprising an aqueous solution containing (a) Ce+4 ions, (b) ruthenium tetroxide and (c) one or more acids selected from the class consisting of methanesulfonic acid and sulfuric acid, and an organic phase containing an acid selected from the class consisting of valeric acid, isovaleric acid, pivalic acid, isobutyric acid, 2-ethylbutyric acid, butyric acid, heptanoic acid, octanoic acid, and mixtures of such acids, and cyclododecene, in which the overall mole ratio of Ce+4 to ruthenium tetroxide in the mixture is greater than 1, and oxidizing cyclododecene in the mixture to dodecanedioic acid at a temperature in the range of about 25 to 85 degrees C.

2. The process of claim 1 in which the ratio of ruthenium tetroxide to cyclododecene in the reaction mixture is greater than 1.

3. The process of claim 1 in which the concentration of $Ce^{+4}$ ion diminishes during the oxidation of the cyclododecene.

4. The process of claim 3 in which the concentration of the $Ce^{+4}$ ion diminishes to a level where the ratio of $Ce^{+4}$ to ruthenium is 1 or less.

5. The process of claim 3 which is followed by a separate step of adding a reducing agent to the mixture to lower the $Ce^{+4}$ ion concentration and the ruthenium tetroxide concentration.

6. The process of claim 1 which includes the additional steps of separating the organic phase from the aqueous phase, and separating dodecanedioic acid from the organic phase.

7. The process of claim 6 in which after separation of the organic phase from the aqueous phase, the aqueous phase is subjected to electrolytic oxidation to regenerate the Ce+4 ions.

8. The process of claim 1 in which the concentration of the ruthenium tetroxide in the mixture is in the range of about 5 to about 1300 parts per million.

9. The process of claim 1 in which the ratio of aqueous phase to organic phase is in the range of 0.5 to 1 to 10 to 1.

10. The process of claim 1 in which the organic phase contains valeric acid.

11. The process of claim 1 in which the aqueous phase contains methanesulfonic acid.

* * * * *